US00PP15783P3

(12) United States Plant Patent
Rubio

(10) Patent No.: US PP15,783 P3
(45) Date of Patent: Jun. 7, 2005

(54) STRAWBERRY PLANT NAMED 'CARMELA'

(50) Latin Name: *Fragaria×ananassa*
Varietal Denomination: Carmela

(75) Inventor: Ignacio Abascal Rubio, Navarra (ES)

(73) Assignee: Plantas de Navarra S.A., Valtierra (ES)

( * ) Notice: Subject to any disclaimer, the term of this patent is extended or adjusted under 35 U.S.C. 154(b) by 49 days.

(21) Appl. No.: 10/678,778

(22) Filed: Oct. 2, 2003

(65) Prior Publication Data

US 2005/0010982 P1 Jan. 13, 2005

(51) Int. Cl.[7] ..... A01H 5/00

(52) U.S. Cl. ..... Plt./208

(58) Field of Search ..... Plt./208

(56) References Cited

U.S. PATENT DOCUMENTS

PP10,960 P 6/1999 Lopez

*Primary Examiner*—Anne Marie Grunberg
(74) *Attorney, Agent, or Firm*—Christie, Parker & Hale, LLP

(57) ABSTRACT

Described is a strawberry variety having inflorescence about level with the foliage and abundant fruit production with early ripening.

10 Drawing Sheets

Botanical classification: The present invention relates to a new *Fragaria×ananassa* Duch. plant.

Varietal denomination: The new plant has the varietal denomination 'Carmela'.

BACKGROUND OF THE INVENTION

The new variety of strawberry was created in a breeding program by crossing two parents; in particular, by crossing as seed parent an undistributed strawberry parent designated 86-032 (not patented) and as pollen parent an undistributed strawberry parent designated 9261 (not patented). Female is a component of a parent collection, from a selection made between plants issued from seeds in a free pollination in a population of different origin. Male is a selection from breeder's program of Planasa. Both parental varieties are proprietary and have not been commercialized, distributed or patented. 'Carmela' can be compared to the female parent 86-032 in that both have conical shaped fruit. However, 'Carmela' differs from the female parent in that the inflorescences of 86-032 are above the foliage whereas the inflorescences of 'Carmela' appear level with the foliage. 'Carmela' can be compared to the male parent 9261 in that both have inflorescences that are level with the foliage. However, 'Carmela' differs from the male parent in that the fruit is conical whereas the male parent has cylindrical shaped fruit.

The resulting seedling of the new variety was grown and asexually propagated by runners in Soria, Spain, 3° W., 42° N., 3000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Carmela'. Among the characteristics which appear to distinguish the new variety from other varieties are a combination of traits which include inflorescence that appears level with the foliage and abundant production of orange red colored, conical shaped, and very firm fruit, medium fruit size, and very early time of ripening (50% of plants with ripe fruits).

COMPARISON TO CLOSEST VARIETY

The new variety is closest to the variety 'Tudnew' (U.S. Plant Pat. No. 10,960), but is distinguished therefrom by the following characteristics possessed by 'Carmela' which are different than, or not possessed by, 'Tudnew' (U.S. Plant Pat. No. 10,960).

1. 'Tudnew' (U.S. Plant Pat. No. 10,960) exhibits a habit of plant flat globose than 'Carmela' exhibits a habit of plant globose.
2. 'Tudnew' (U.S. Plant Pat. No. 10,960) shows a leaf color of upper side (RHS green group near 138B to 138A) less dark than 'Carmela' (RHS green group near 131B to 135A).
3. Length/width ratio of the terminal leaflet in 'Tudnew' (U.S. Plant Pat. No. 10,960) is as long as broad, than in 'Carmela' it is longer than broad.
4. In 'Tudnew' (U.S. Plant Pat. No. 10,960) the position of the inflorescence relative to foliage is above. In 'Carmela' it is level with.
5. The attitude of hairs in 'Tudnew' (U.S. Plant Pat. No. 10,960) is slightly outwards, than in 'Carmela' it is upwards.
6. The fruit size of 'Tudnew' (U.S. Plant Pat. No. 10,960) is more large than of 'Carmela'.
7. 'Tudnew' (U.S. Plant Pat. No. 10,960) shows a red fruit color (RHS red group near 42C to 42A), whereas in 'Carmela' it is an orange red fruit color (RHS orange red group near 33A to 34A).

8. The predominant shape of fruits of 'Tudnew' (U.S. Plant Pat. No. 10,960) is biconical, whereas in 'Carmela' it is conical.

The differences in the leaf color of upper side of the new variety and 'Tudnew' (U.S. Plant Pat. No. 10,960) are shown in FIGS. 2 and 3. The differences in the fruits of the new variety and 'Tudnew' (U.S. Plant Pat. No. 10,960) are shown in FIGS. 7, 8, and 9,10. These differences are maintained during the harvest season.

9. 'Tudnew' (U.S. Plant Pat. No. 10,960) shows a firmness fruit slightly more than 'Carmela' fruit.
10. Precocity in 'Tudnew' (U.S. Plant Pat. No. 10,960) is smaller than in 'Carmela'.

BRIEF DESCRIPTION OF ILLUSTRATIONS

The accompanying photographs show typical specimens of the new variety, designated 98.08V.134 in the illustrations, including fruit, foliage and flower, in color as nearly true as it is reasonably possible to make in color illustrations of this character.

The plants depicted in the drawings were planted in October in the farm of La Mogalla in Cartaya (Huelva), Spain, about 7° W, 37° N, 45 feet elevation.

Drawings were taken in April: minimum temperate about 16° C. to 18° C., maximum temperate about 31 to 33° C.

Figure 1:
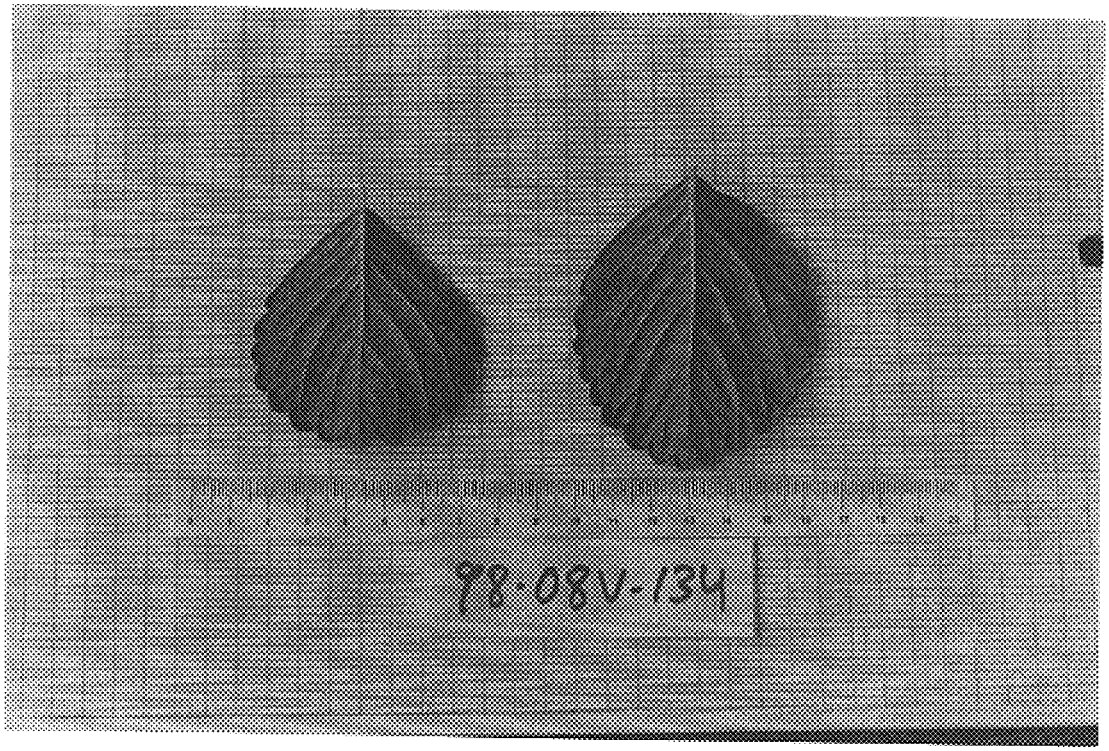
FIG. 1 shows the undersurface of a typical terminal leaflet of the new variety (designated 98.08V.134) with a shape of base obtuse and in which the length/width ratio is longer than broad.
Figure 2:
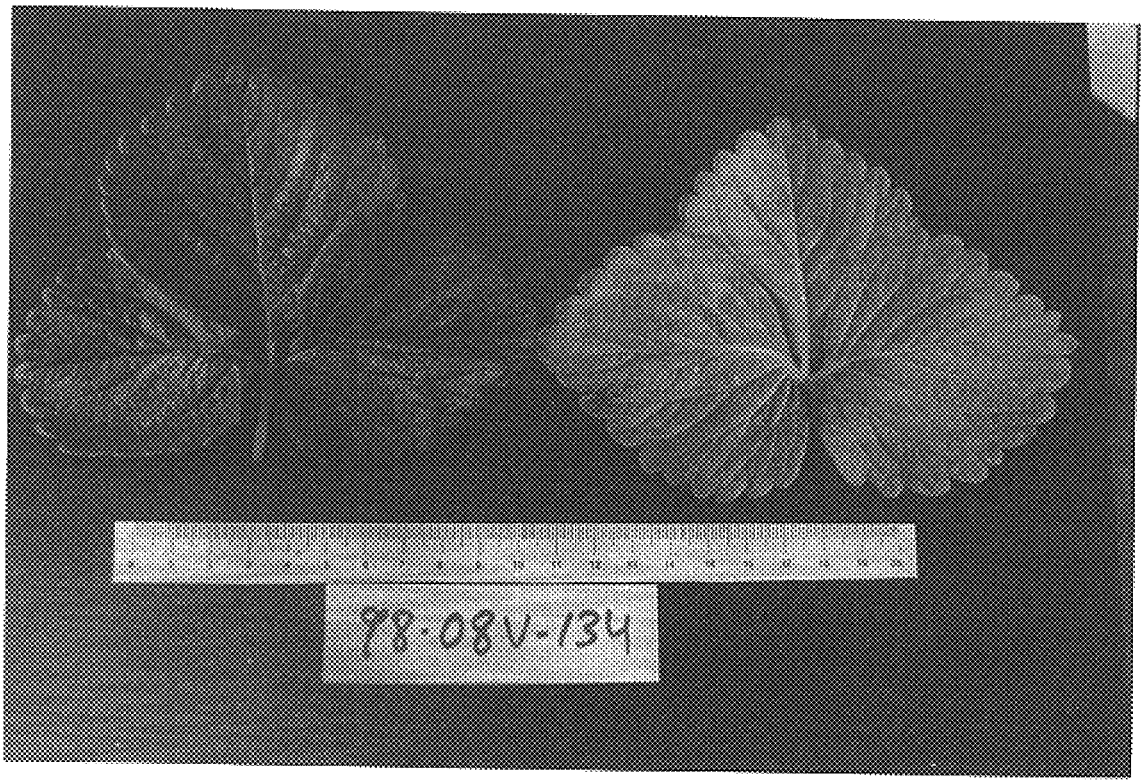
FIG. 2 shows the top and undersurface of a complete leave of the new variety (designated 98.08V.134).
Figure 3:
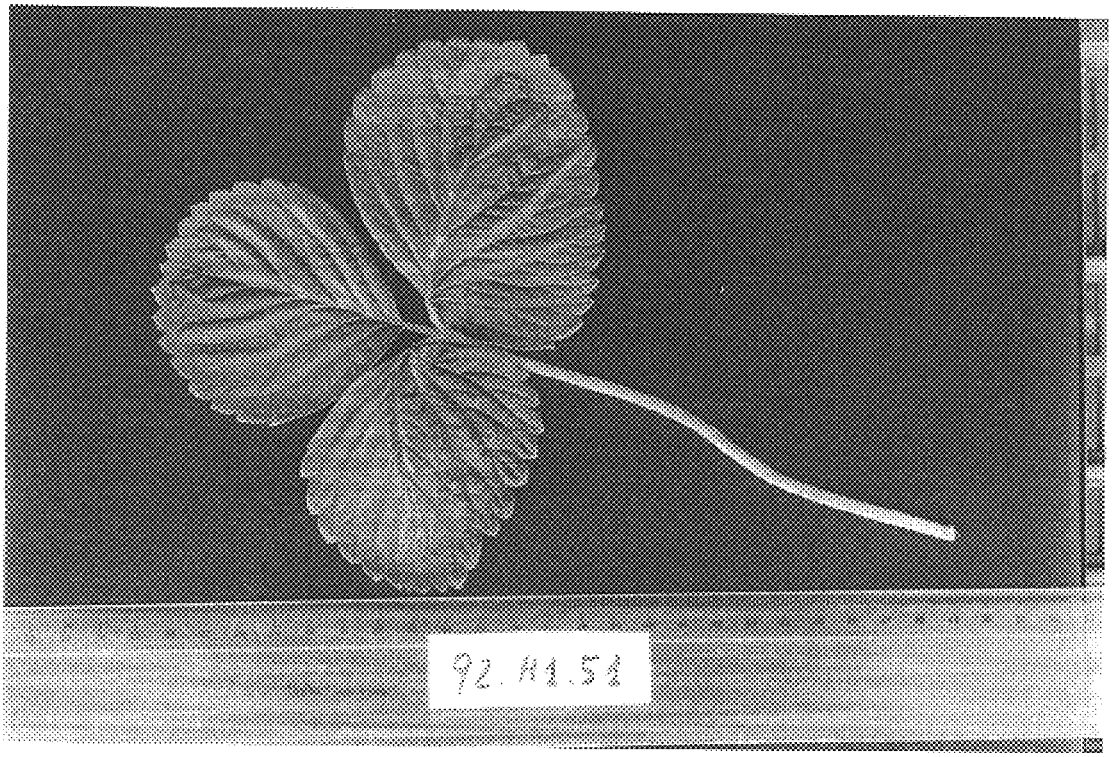

FIG. 3 shows the top of a complete leave of 'Tudnew' (U.S. Plant Pat. No. 10,960) (designated 92.H1.51). In them we can see that the leaf color of upper side of 'Tudnew' (U.S. Plant Pat. No. 10,960) is less dark than 'Carmela'.

Figure 4:
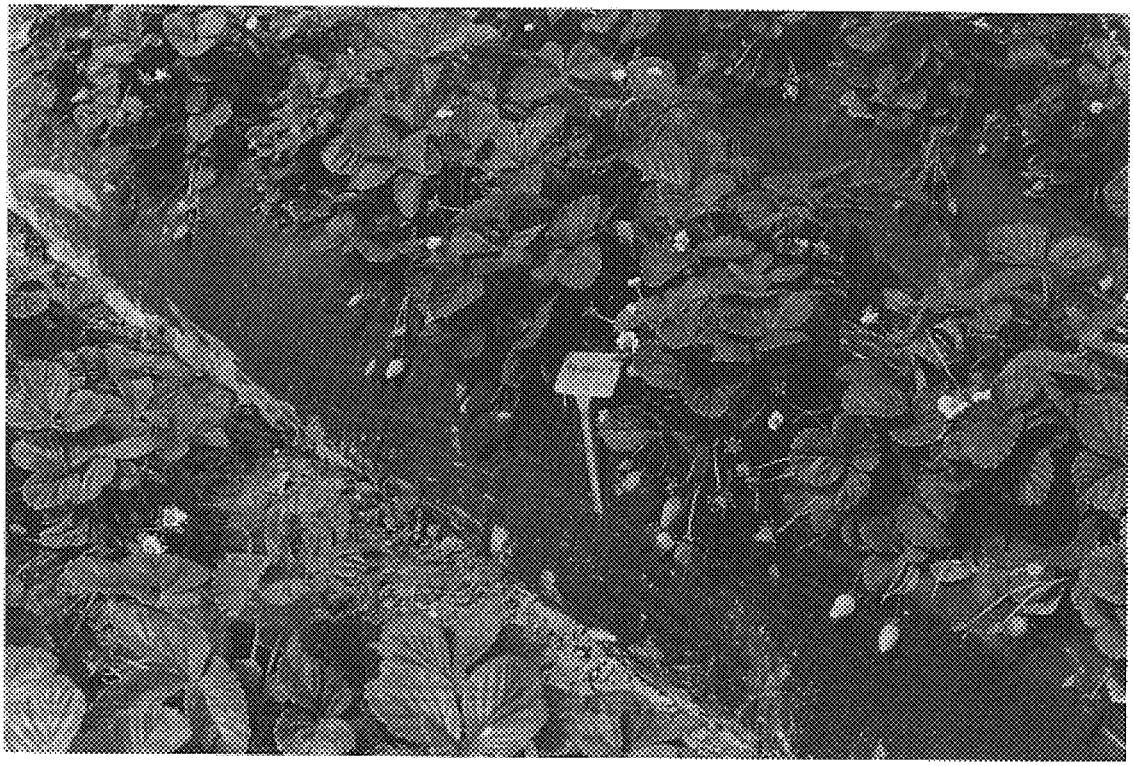
Figure 5:
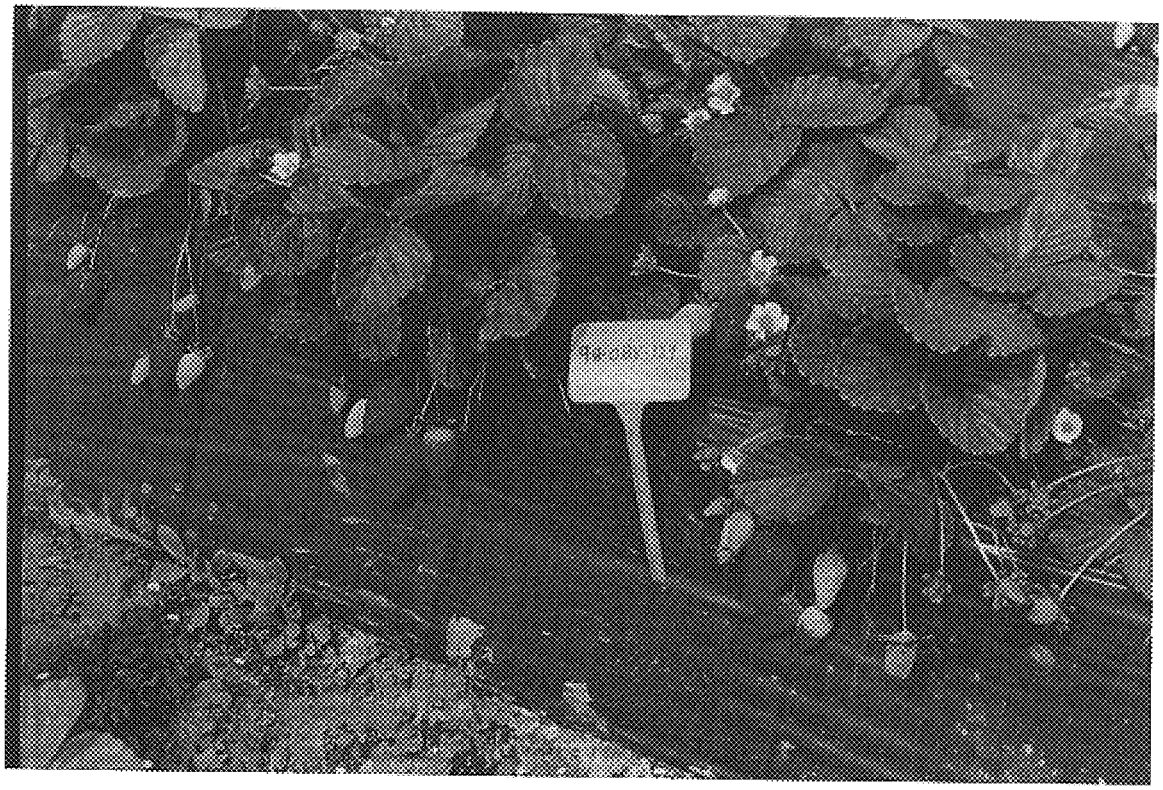

FIGS. 4 and 5 show the fruit against a background of the top surface of the foliage of the new variety (designated 98.08V.134).

Figure 6:
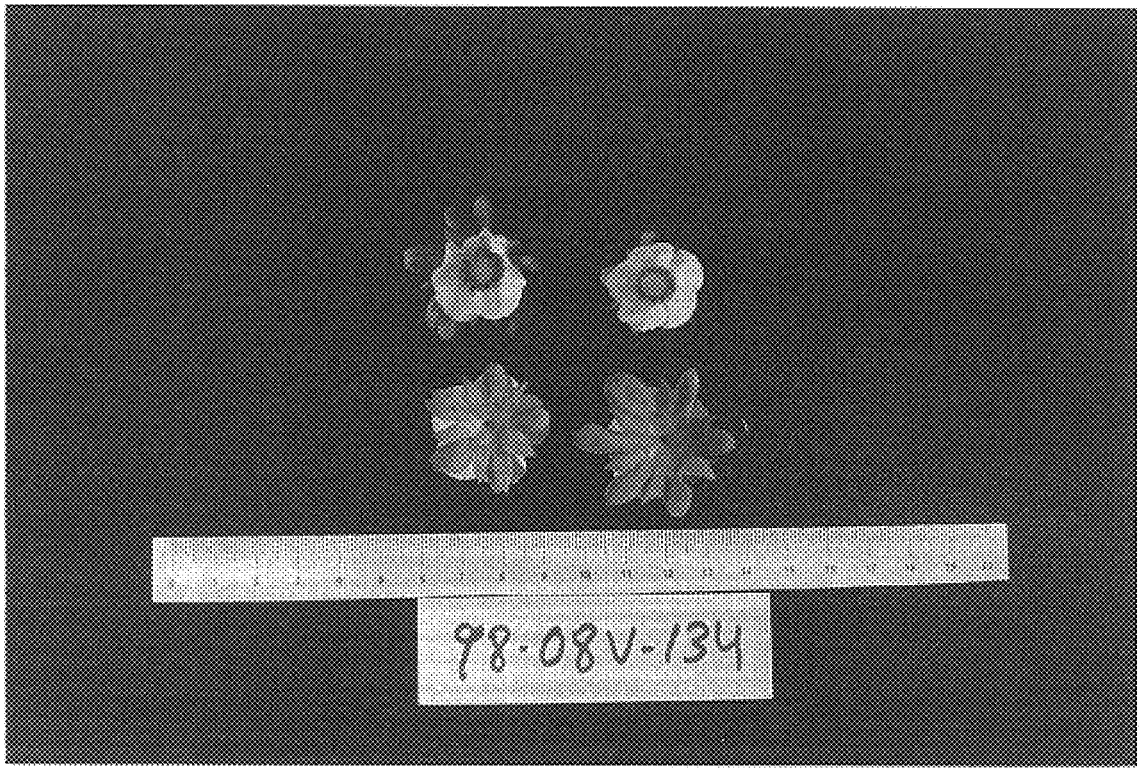

FIG. 6 shows the flower and reproductive organs of the new variety (designated 98.08V.134).

Figure 7:
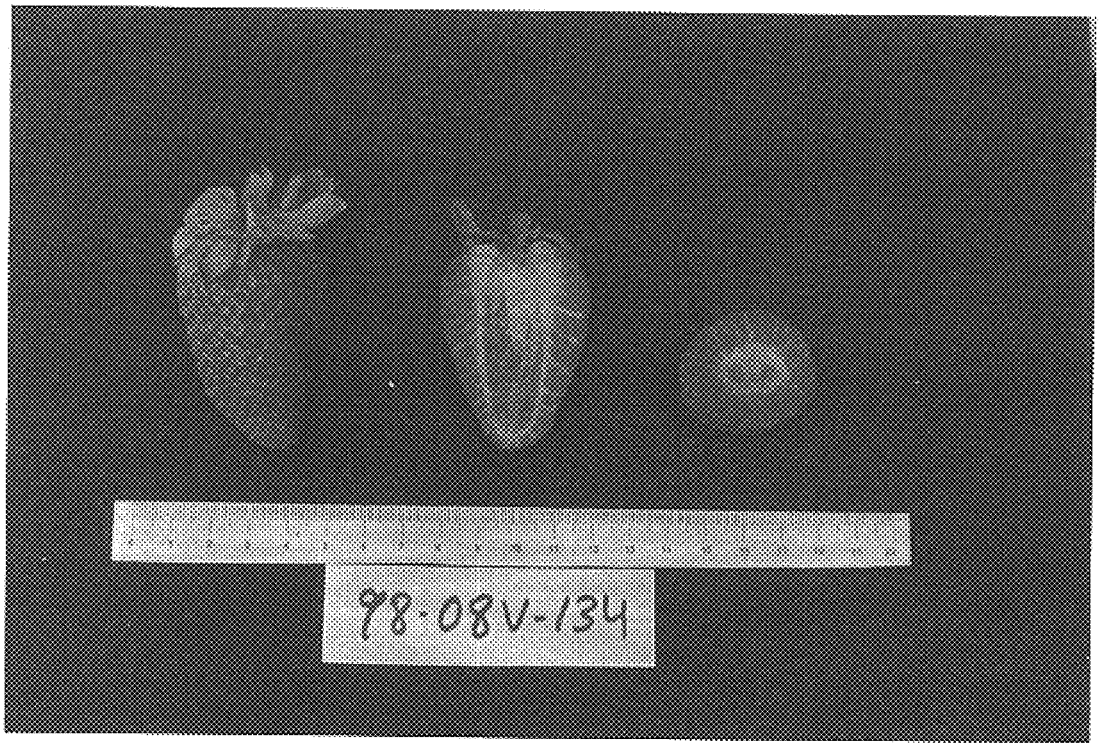
Figure 8:
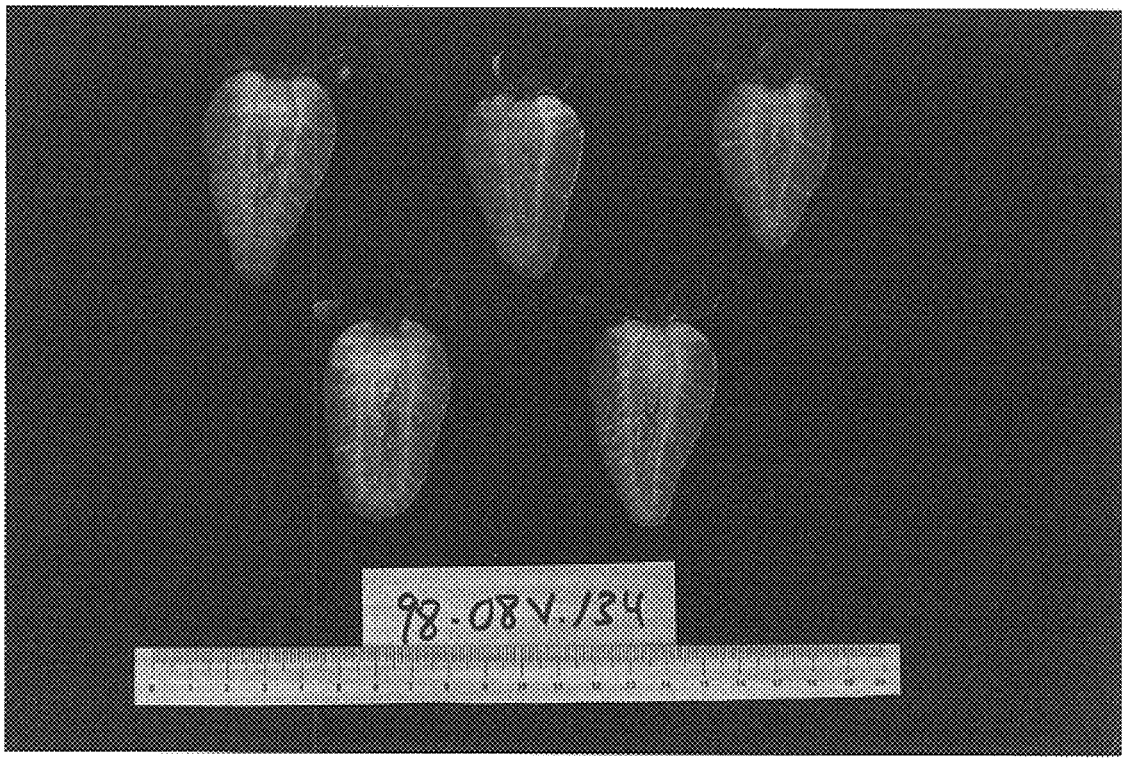

FIGS. 7 and 8 show typical fruit of the new variety (designated 98.08V.134) whole, sliced and in cross section, illustrating the typical flesh and flesh coloration, conspicuous core and core cavity, conical shape and orange red fruit color.

Figure 9:
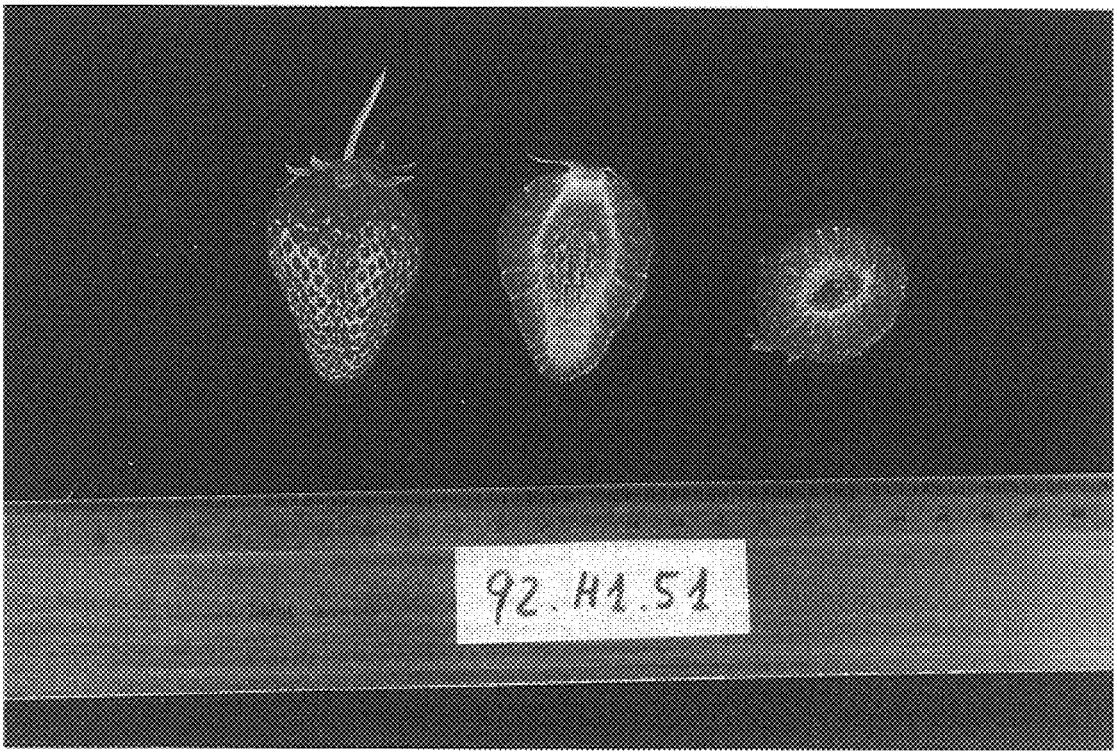
Figure 10:
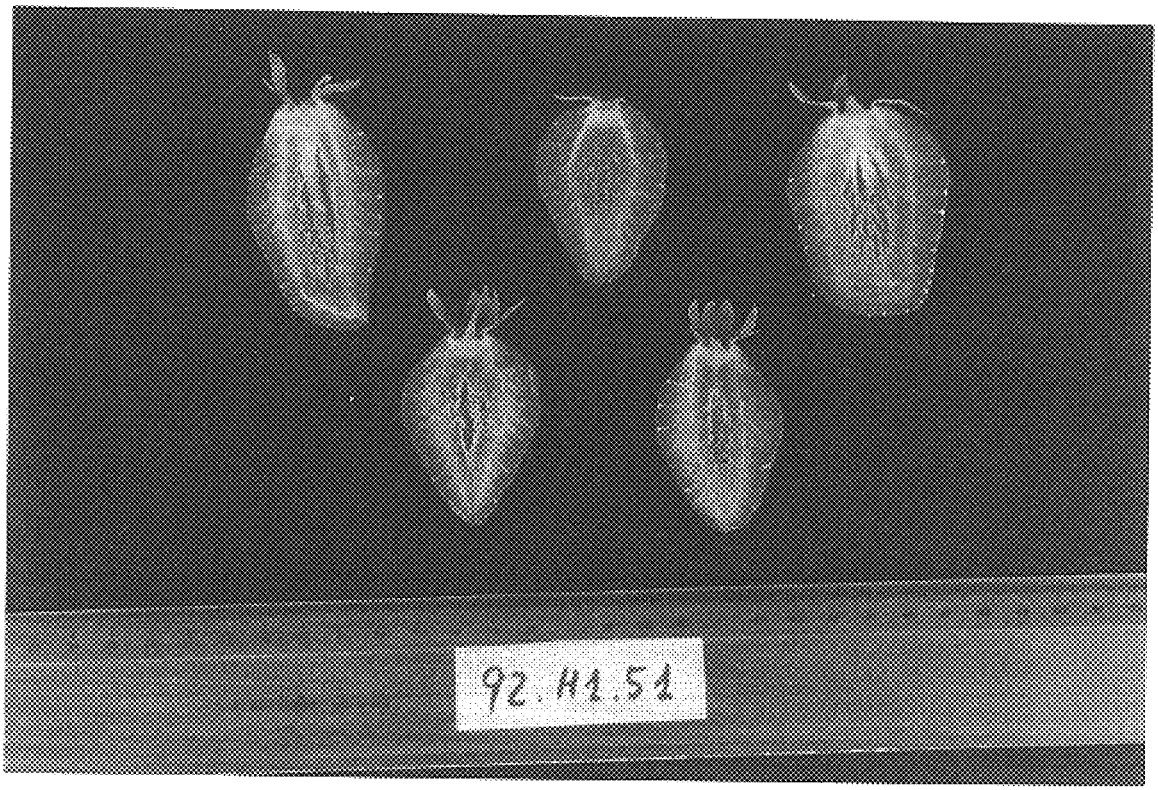

FIGS. 9 and 10 show typical fruit of the 'Tudnew' (U.S. Plant Pat. No. 10,960) (designated 92.H1.51) whole, sliced and in cross-section, illustrating the typical flesh and flesh coloration, conspicuous core and core cavity, biconical shape and red fruit color.

DESCRIPTION OF THE NEW VARIETY

The following detailed description of the new variety is based upon observations taken of plants and fruits grown "under glass", i.e., under tunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPAGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'Carmela' is a short day variety that needs an induction to flowering by chilling, such as occurs at a high elevation nursery (fresh plant) or with cold storage (referred to as a frigo). Usually a short time is sufficient. 'Carmela' is self-fertile. It produces large quantity of pollen throughout the seasons and pollination is generally good as there are very few malformed fruit.

Production: Plants described are from high elevation nursery.

Description taken in Cartaya (Huelva), Spain of plants planted in October 2002.

Number of repetitions: 2

Plants per repetition: 225

Comparison with 'Tudnew' (U.S. Plant Pat. No. 10,960): The new variety is compared with 'Tudnew' (U.S. Plant Pat. No. 10,960) (designated 92.H1.51) in FIG. 2 and FIG. 3 and FIG. 7 and FIG. 8 and FIG. 9 and FIG. 10.

| | Accumulated production of 1st quality fruit (g/plant) | | | |
|---|---|---|---|---|
| Variety | 21-Fb | 28-Mr | 25-Ap | 15-My |
| MILSEI | 12 | 98 | 451 | 802 |
| CAMAROSA | 15 | 96 | 519 | 1035 |
| TUDNEW | 23 | 102 | 481 | 936 |
| CARMELA | 48 | 168 | 458 | 809 |

| Variety | 1st + 2nd Quality Fruit | Total | Weight (g/fruit) |
|---|---|---|---|
| MILSEI | 802 + 109 | 911 | 22 –21 |
| CAMAROSA | 1035 + 183 | 1218 | 24 –23 |
| TUDNEW | 936 + 104 | 1040 | 24 –23 |
| CARMELA | 809 + 90 | 899 | 22 –21 |

| | | | TOTAL | |
|---|---|---|---|---|
| Variety | 1st quality | 2nd quality | (1st quality + 2nd quality) | % 2nd quality |
| MILSEI | 802 | 109 | 911 | 12 |
| CAMAROSA | 1035 | 183 | 1218 | 15 |
| TUDNEW | 936 | 104 | 1040 | 10 |
| CARMELA | 809 | 90 | 899 | 10 |

Production total, to 15 May, of First Quality Fruit (1st quality) and Second Quality Fruit (2nd quality) in g/plant
% 2nd quality = 2nd quality TOTAL × 100

| Weight (g/Fruit) at two dates: 28 March and 15 May | | |
|---|---|---|
| WEIGHT (g/fruit) | 28 March | 15 May |
| MILSEI | 22 | 21 |
| CAMAROSA | 24 | 23 |
| TUDNEW | 24 | 23 |
| CARMELA | 22 | 21 |

WEIGHT is shown as the average weight per fruit in First Quality Fruits.

FRUIT ANALYSIS

| | CAMAROSA | CARMELA (98.08V.134) | MILSEI | TUDNEW |
|---|---|---|---|---|
| Firmness (KG) | 0.60 | 0.86 | 0.34 | 0.98 |
| Humidity & Volatile Matter (%) | 91.10 | 90.90 | 92.00 | 91.80 |
| Dry Matter (%) | 8.90 | 9.10 | 8.00 | 8.20 |
| PH (to 20°) | 3.50 | 3.60 | 3.60 | 3.60 |
| Acidity as Anhydride Citric (%) | 1.10 | 1.10 | 1.00 | 1.00 |
| Soluble Solids (°Brix) | 7.90 | 8.10 | 7.20 | 6.70 |
| Maturity Index | 7.30 | 7.70 | 7.10 | 6.80 |
| Content in Ascorbic Acid (ppm) | 670 | 600 | 560 | 600 |
| Dominant Tonality (nm) | 495 | 495 | 500 | 500 |
| Luminosity: Transmittance to 460 nm | 11.10 | 38.60 | 20.90 | 41.30 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the weight of the residual left from the trituration of the fruit after the drying process at a temperature of 103° C.$^{+}$2° C. until reaching constant weight.

$$(\%)\ \text{Dry Matter} = \frac{\text{Weight Dry Matter}}{\text{Weight Fresh Matter}} \times 100$$

Humidity & Volatile Matter: Represents the content in volatile matters and water of the fruits.

$$(\%)\ \text{Humidity \& Volatile Matter} = 100 - \%\ \text{Dry Matter}$$

Maturity Index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety.

Variety: Carmela. Breeder Ref. 98.08V.134.

Classification: *Fragaria×ananassa* Duch.

Plant:

*Habit.*—Globose.

*Density.*—Medium.

*Vigor.*—Medium.

*Height.*—About 21 cm.

*Width.*—About 22 cm.

Leaf:

*Upper side.*—RHS green group color (near 131B to 135 A).

*Underside.*—RHS green group color (near 143D to 138D).

*Length.*—About 10 cm.

*Width — section.*—About 13 cm. to 14 cm.

*Leaf surface ondulation or blistering.*—Very strong.

*Number of leaflets.*—Three only.

Leaf stem characteristics:

*Color.*—RHS green group (near 138D).

*Position of hairs.*—Upwards.

*Length.*—About 12 cm.

Terminal leaflet:

*Length/width ratio.*—Longer than broad.

*Length.*—About 7,5 cm.

*Width.*—About 6 cm.

*Shape of base.*—Obtuse.

*Shape of teeth.*—Crenate.

Petiole:

*Position of hairs.*—Upwards.

*Length.*—About 12 cm.

Stipule:

*Anthocyanin coloration.*—Strong. Color — RHS greyed-red group coloration (near 178C to 179A).

Stolons:

*Number.*—Many, about 9 to 10.

*Thickness.*—Medium, about 3.2 mm.

*Pubescence.*—Medium.

*Color.*—RHS green group (near 138D to 142D).

Inflorescence:

*Position relative to foliage.*—Level with.

Flower:

*Size.*—Medium.

*Size of calyx relative to corolla.*—Larger.

*Spacing of petals.*—Overlapping.

Flower characteristics:

*Diameter primary flowers.*—About 2.0–2.5 cm.

*Diameter secondary flowers.*—About 2.0 cm.

*Number of petals.*—Normally about 6. No significant fragrance.

*Time from bloom to mature fruit* (*in Huelva, Spain*).—About 33 to 37 days.

*Stamens.*—Numerous with pollen present, fertile and abundant. Length — approximately 4 mm. Color — RHS white group (near 155D to 155C).

*Anthers.*—Generally average in size. Color — RHS yellow group (near 12B to 13B) and darkening with advanced maturity.

*Pollen.*—Fertile and abundant. Color — RHS yellow orange group (near 14B to 15B).

*Pistils.*—Numerous, generally average in size. Color — RHS yellow group (near 12B to 13B).

Petal:

*Length/width ratio.*—As long as broad.

Fruiting truss:

*Attitude.*—Semi-erect.

Fruit:

*Ratio of length/maximum width.*—Much longer than broad.

*Color.*—RHS orange red group (near 33A to 34A).

*Peduncle length of inflorescence stem.*—Primary fruit about 9 to 11 cm, secondary fruit about 6 to 7 cm, color near 138D.

Primary fruit:

*Length.*—About 5.0–5.5 cm.

*Width.*—About 3.0–3.5 cm.

Secondary fruit:

*Length.*—About 4.5–5.0 cm.

*Width.*—About 2.5–3.0 cm.

*Size.*—Medium.

*Predominant shape.*—Conical.

*Difference in shapes between primary and secondary fruits.*—Slight.

*Band without achenes.*—Medium.

*Color of achenes.*—RHS orange red group (near 33C to 33B).

*Unevenness of surface.*—Absent or very weak.

*Evenness of color.*—Even.

*Glossiness.*—Medium.

*Insertion of achenes.*—Below surface.

*Insertion of calyx.*—Set above fruit.

*Pose of the calyx segments.*—Reflexed.

*Size of calyx in relation to fruit diameter.*—Much larger.

*Adherence of calyx.*—Very strong.

*Firmness.*—Firm.

*Color of flesh.*—RHS orange red group (near 34C to 34B), lightening toward center.

*Distribution of red color of flesh.*—Marginal and central.

*Hollow center.*—Weakly expressed.

*Sweetness.*—Strong.

*Acidity.*—Medium.

*Time of flowering (50% of plants at first flower).*—Very early.

*Time of ripening (50% of plants with ripe fruits).*—Very early.

*Type of bearing.*—Not remontant.

*Chilling.*—Weak.

*Planting date.*—Oct. 30, 2002.

*10% flowering.*—Dec. 23, 2002.

*First mature fruits.*—Jan. 26, 2003.

*Maturity (15–20 gms/plant).*—Feb. 8, 2003.

Time of flowering data: Date of planting: Oct. 30, 2002 in the farm of La Mogalla, in Cartaya (Huelva), Spain, about 7° W., 37° N, 45 feet elevation. 10% flowering occurs about Dec. 23, 2002 with first mature fruit about Jan 26, 2003 and maturity (15–20 g/plant) about Feb. 8, 2003.

Time of flowers (50% of plants at first flower): About Dec. 30, 2002.

Storage qualities: 'Carmela' fruit maintain their quality characteristics when keeping them in a frigo chamber at temperatures of about 2° C. during 48 hours. The fruit's color remains substantially the same.

Time of ripening: After planting as aforesaid, plants are grown in raised beds under tunnel (small tunnel with small holes in plastic walls). Water and fertilizer were applied through drip irrigation. Time of ripening (50% of plants with ripe fruit) is about Jan. 31, 2003. First mature fruit is about Jan. 26, 2003 and maturity (15–20 gms/plant) is about Feb. 8, 2003.

General: The growing period in Huelva, Spain, where the observations were made, is between about December,10 and May,15 of each year, with a maximum production at about mid-April. 'Carmela' is a short variety that benefits from induction to flowering by chilling, usually a few hours are sufficient, preferably at temperatures of 7° C. or less. Normally, the minimum number of hours is accumulated in the field during several days.

Disease resistance: No particular sensitivity to any disease or parasite has been observed for 'Carmela'.

I claim:

1. A new and distinct strawberry plant of the variety substantially as shown and described.

* * * * *